US00PP14168P29

(12) United States Plant Patent
Kromhout

(10) Patent No.: US PP14,168 P2
(45) Date of Patent: Sep. 23, 2003

(54) HYDRANGEA PLANT NAMED 'DARDOM'

(75) Inventor: Woulter Kromhout, Leersum (NL)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 10/232,892

(22) Filed: Aug. 31, 2002

(51) Int. Cl.[7] ..... A01H 5/00

(52) U.S. Cl. ..... Plt./250

(58) Field of Search ..... Plt./250

(56) References Cited

PUBLICATIONS http://www.environmental–care.com/plants/annabelle-.html.* http://www.colorchoiceplants.com/white_dome.htm.*

UPOV ROM GTITM Computer Database GTI JOVVE Reversal Software.*

* cited by examiner

*Primary Examiner*—Bruce R. Campell
*Assistant Examiner*—W C Haas
(74) *Attorney, Agent, or Firm*—C. A. Whealy

(57) ABSTRACT

A distinct cultivar of Hydrangea plant named 'Dardom', characterized by its large and vigorous growth habit; upright and rounded plant habit; strong stems; large durable leaves; large dome-shaped inflorescences; and inflorescences with large sterile flowers and numerous small fertile flowers.

1 Drawing Sheet

Botanical classification/cultivar designation: *Hydrangea arborescens* cultivar Dardom.

BACKGROUND OF THE INVENTION

The present Invention relates to a new and distinct cultivar of Hydrangea plant, botanically known as *Hydrangea arborescens,* and hereinafter referred to by the cultivar name Dardom.

The new Hydrangea originated from a chance cross-pollination in 1997 of two unidentified selections of *Hydrangea arborescens,* not patented. The cultivar Dardom was discovered and selected by the Inventor as a single plant within the progeny of the stated cross-pollination in a controlled environment in Essen, Belgium.

Asexual reproduction of the new cultivar by softwood cuttings taken at Leersum, The Netherlands, since spring, 1999, has shown that the unique features of this new Hydrangea are stable and reproduced true to type in successive generations.

SUMMARY OF THE INVENTION

Plants of the cultivar Dardom have not been observed under all possible environmental conditions. The phenotype may vary somewhat with variations in environment such as temperature and light intensity without, however, any variance in genotype.

The following traits have been repeatedly observed and are determined to be the unique characteristics of 'Dardom'. These characteristics in combination distinguish 'Dardom' as a new and distinct cultivar:

1. Large and vigorous growth habit.
2. Upright and rounded plant habit, strong stems.
3. Large durable leaves.

4. Large dome-shaped inflorescences.
5. Inflorescences with large sterile flowers and numerous small fertile flowers.

Plants of the new Hydrangea differ from plants of parent selections and other selections of *Hydrangea arborescens* known to the inventor in the following characteristics:

1. Plants of the new Hydrangea are taller and more vigorous than other known selections of *Hydrangea arborescens* known to the inventor.
2. Plants of the new Hydrangea are more freely branching than other selections of *Hydrangea arborescens* known to the inventor.
3. Plants of the new Hydrangea have larger, healthier and more durable foliage than other selections of *Hydrangea arborescens* known to the inventor.
4. Plants of the new Hydrangea have larger inflorescences with more flowers per inflorescence than other selections of *Hydrangea arborescens* known to the inventor.

Plants of the new Hydrangea can be compared to plants of the *Hydrangea arborescens* cultivar Annabelle, not patented. In side-by-side comparisons conducted in Grand Haven, Mich., plants of the new Hydrangea differed from plants of the cultivar Annabelle in the following characteristics:

1. Plants of the new Hydrangea were taller and more vigorous than plants of the cultivar Annabelle.
2. Plants of the new Hydrangea were more freely branching than plants of the cultivar Annabelle.
3. Plants of the new Hydrangea had stronger stems than plants of the cultivar Annabelle.
4. Plants of the new Hydrangea had broader, healthier and more durable foliage than plants of the cultivar Annabelle.
5. Plants of the new Hydrangea had dome-shaped inflorescences whereas plants of the cultivar Annabelle had globose-shaped inflorescences.

6. Plants of the new Hydrangea were more freely flowering than plants of the cultivar Annabelle.
7. Flowers of plants of the new Hydrangea were mostly fertile whereas flowers of plants of the cultivar Annabelle were mostly sterile.

BRIEF DESCRIPTION OF THE PHOTOGRAPHS

The accompanying colored photographs illustrate the unique appearance of the new cultivar, showing the colors as true as it is reasonably possible to obtain in colored reproductions of this type. Colors in the photographs may differ from the color values cited in the detailed botanical description which accurately describe the colors of the new Hydrangea.

The photograph at the top of the sheet is a close-up view of a inflorescence of a typical plant of 'Dardom'.

The photograph at the bottom of the sheet comprises a side perspective view of a typical plant of 'Dardom' grown in the landscape.

DETAILED BOTANICAL DESCRIPTION

In the following description, color references are made to The Royal Horticultural Society Colour Chart, 1995 Edition, except where general terms of ordinary dictionary significance are used. Plants used in the aforementioned photographs and in the following description were grown in Grand Haven, Mich., in ground beds in an outdoor nursery and under conditions which closely approximate commercial production conditions. Plants were about three years old when the photographs and description were taken. The photographs and description were taken during late spring and early summer.

Botanical classification: *Hydrangea arborescens* cultivar Dardom.

Parentage:

*Male, or pollen, parent.*—Unidentified *Hydrangea arborescens* selection, not patented.

*Female, or seed, parent.*—Unidentified *Hydrangea arborescens* selection, not patented.

Propagation:

*Type cutting.*—By softwood cuttings.

*Time to initiate roots.*—About 10 days at 25° C.

*Time to produce a rooted cutting or liner.*—About 70 days at 25° C.

*Root description.*—Fine; cream-colored.

*Rooting habit.*—Freely branching.

Plant description:

*Form/growth habit.*—Upright and rounded plant habit; bushy perennial shrub. Tall and vigorous.

*Usage.*—Appropriate for one to three-gallon containers.

*Plant height, soil level to top of plant.*—About 150 cm.

*Plant diameter or area of spread.*—About 100 cm.

*Branching habit.*—When pinched, freely branching with potentially about 99 lateral branches per plant.

*Lateral branches.*—Length: About 100 cm. Diameter: About 7 mm. Internode length: About 18 cm. Texture: Glabrous. Color: 146C.

*Foliage description.*—Leaves large, simple, opposite and durable. Quantity per lateral branch: Typically about 22. Length: About 16 cm. Width: About 13.5 cm. Shape: Broadly ovate. Apex: Obtuse to acute. Base: Cordate to obtuse. Margin: Dentate to serrate. Texture: Upper surface: Glabrous. Lower surface: Slightly pubescent. Venation pattern: Pinnate. Color: Young foliage, upper surface: 146A. Young foliage, lower surface: 196A. Mature foliage, upper surface: 136A. Mature foliage, lower surface: 191A. Venation, upper surface: 136C. Venation, lower surface: 191B. Petiole: Length: About 7 cm. Diameter: About 4 mm. Color: 146B.

Flower description:

*Flower type and habit.*—Single fertile and sterile flowers arranged on terminal corymbs; corymbs large and semi-hemispherical or dome-shaped. Sterile flowers with large showy sepals and without petals and reproductive organs. Fertile flowers with petals, sepals and reproductive organs. Flowers persistent. Inflorescences slightly fragrant.

*Natural flowering season.*—Continuously flowering from early July to mid-August in Grand Haven, Mich.

*Flower longevity.*—Sterile flowers last about six weeks on the plant; fertile flowers last about five weeks on the plant.

*Quantity of flowers.*—Freely flowering; about 16 sterile flowers and about 1863 fertile flowers per corymb.

*Corymb diameter.*—About 20 cm by 15 cm.

*Corymb height.*—About 10 cm.

*Flower diameter.*—Fertile flowers: About 3 to 4 mm. Sterile flowers: About 2 cm.

*Flower depth (height).*—Fertile flowers: About 2 to 3 mm. Sterile flowers: About 3 mm.

*Flower buds (fertile and sterile flowers).*—Length: About 2 mm. Diameter: About 2 mm. Shape: Obovate. Color: 144B.

*Petals (petals present only on fertile flowers; sterile flowers do not have petals).*—Arrangement: About five. Length: About 3 mm. Width: About 2 mm. Shape: Lanceolate. Apex: Acute. Base: Attenuate. Margin: Entire. Texture, upper and lower surfaces: Smooth, glabrous. Color: When opening, upper and lower surfaces: 143D. Fully opened, upper and lower surfaces: 155D.

*Sepals.*—Quantity per flower: Fertile flowers: About five, fused into a calyx. Sterile flowers: About three or four. Length: Fertile flowers: About 2 mm. Sterile flowers: About 1 cm. Width: Fertile flowers: About 1 mm. Sterile flowers: About 8 mm. Shape: Fertile flowers: Connate. Sterile flowers: Ovate. Apex: Fertile flowers: Acute. Sterile flowers: Acute. Base: Fertile flowers: Fused. Sterile flowers: Attenuate. Margin: Fertile flowers: Entire. Sterile flowers: Entire. Texture, fertile and sterile flowers, upper and lower surfaces: Smooth, glabrous. Color: Fertile flowers: When opening and fully opened, upper and lower surfaces, 144B. Sterile flowers: When opening, upper and lower surfaces: 157B. Fully opened, upper and lower surfaces: 155D; color becoming closer to 143B with subsequent development.

*Pedicels.*—Angle: Fertile flowers: About 20 to 40° from vertical. Sterile flowers: About 90 to 160° from vertical. Strength, fertile and sterile flowers: Strong. Length, fertile and sterile flowers: About 1.5 cm. Color: Fertile flowers: 144B. Sterile flowers: 155D.

*Reproductive organs (reproductive organ present only on fertile flowers; sterile flowers do not have reproductive organs).*—Stamens: Quantity per flower: About ten. Anther shape: Round. Anther length:

About 1 mm. Anther color: 162D. Pollen amount: Scarce. Pollen color: 155B. Pistils: Pistil quantity per flower: Two, fused. Pistil length: About 1 mm. Stigma shape: Two-lobed. Stigma color: 4D. Style length: About 1 mm. Style color: 4D. Ovary color: 144B. Seed: Minute, dust-like.

Disease/pest resistance: Under commercial production conditions, plants of the new Hydrangea have not been observed to be resistant to pathogens or pests common to Hydrangea.

Weather tolerance: Plants of the new Hydrangea have been shown to be tolerant to temperatures ranging from −30 to 33° C. Flowers of plants have exhibited excellent tolerance to wind and rain.

It is claimed:

1. A new and distinct cultivar of Hydrangea plant named 'Dardom', as illustrated and described.

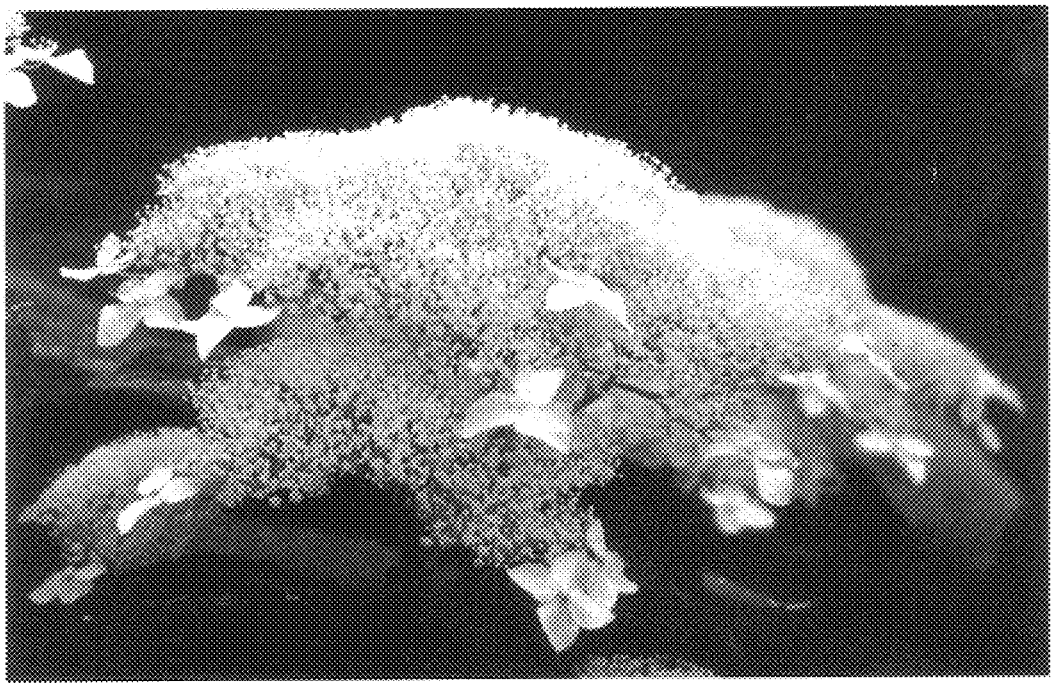
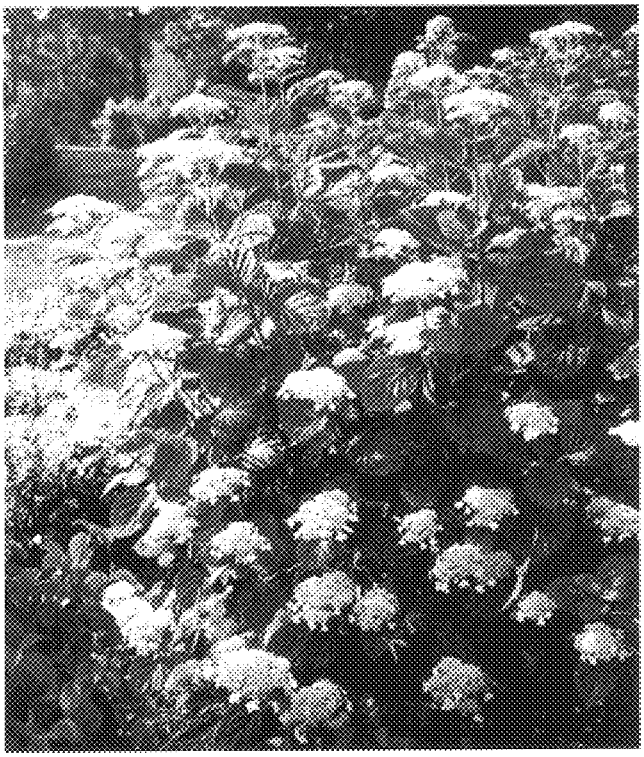

* * * * *